United States Patent
Hasegawa et al.

(10) Patent No.: US 8,192,982 B2
(45) Date of Patent: Jun. 5, 2012

(54) TISSUE CULTURE MICROSCOPE APPARATUS

(75) Inventors: Kazuhiro Hasegawa, Tokyo (JP); Akitsugu Kagayama, Tokyo (JP); Atsuhiro Tsuchiya, Tokyo (JP); Ryuichi Hirano, Tokyo (JP); Kenichi Koyama, Kanagawa (JP); Hideaki Endo, Tokyo (JP)

(73) Assignee: Olympus Corporation, Tokyo (JP)

( * ) Notice: Subject to any disclaimer, the term of this patent is extended or adjusted under 35 U.S.C. 154(b) by 1071 days.

(21) Appl. No.: 11/522,730

(22) Filed: Sep. 18, 2006

(65) Prior Publication Data

US 2007/0065936 A1    Mar. 22, 2007

(30) Foreign Application Priority Data

Sep. 22, 2005   (JP) ................... 2005-276205
Jul. 31, 2006   (JP) ................... 2006-208876

(51) Int. Cl.
*C12M 1/00*    (2006.01)
*C12M 3/00*    (2006.01)
*C12M 1/34*    (2006.01)

(52) U.S. Cl. ............... 435/303.1; 435/288.7; 435/307.1; 435/809; 435/309.1; 435/303.3; 422/939; 73/863.01; 73/864.22; 73/864.24

(58) Field of Classification Search ............... 435/307.1, 435/303.1, 288.7, 809, 309.1, 303.3; 422/939; 73/863.01, 864.22, 864.24
See application file for complete search history.

(56) References Cited

U.S. PATENT DOCUMENTS

| | | | |
|---|---|---|---|
| 5,348,883 A * | 9/1994 | Togawa ....................... | 435/287.3 |
| 5,432,085 A * | 7/1995 | Warren et al. ............... | 435/286.4 |
| 7,415,144 B2 | 8/2008 | Imaizumi et al. | |
| 2002/0155487 A1 * | 10/2002 | Greenberger et al. ............ | 435/6 |
| 2003/0003022 A1 * | 1/2003 | Tamura et al. ................... | 422/99 |
| 2003/0228695 A1 | 12/2003 | Nakamura et al. | |
| 2004/0064013 A1 | 4/2004 | Attias | |
| 2005/0032199 A1 | 2/2005 | Takahashi | |
| 2005/0174085 A1 | 8/2005 | Yuri | |
| 2006/0275888 A1 * | 12/2006 | Hibino et al. ............... | 435/286.2 |
| 2007/0148764 A1 * | 6/2007 | Suzuki et al. ............... | 435/293.1 |

FOREIGN PATENT DOCUMENTS

| | | |
|---|---|---|
| EP | 1 564 575 A1 | 8/2005 |
| JP | 58-155087 A | 9/1983 |
| JP | 3-50896 U | 5/1991 |
| JP | 2001-149062 A | 6/2001 |
| JP | 2003-210157 A | 7/2003 |
| JP | 2003-325161 A | 11/2003 |
| JP | 2005-102538 A | 4/2005 |
| JP | 2006-011415 A | 1/2006 |
| WO | WO-2004/090093 A1 * | 10/2004 |
| WO | WO-2005/059091 A1 * | 6/2005 |

OTHER PUBLICATIONS

Japanese Office Action dated Nov. 22, 2011 (and English translation thereof) in counterpart Japanese Application No. 2006-208876.

* cited by examiner

*Primary Examiner* — Nathan Bowers
(74) *Attorney, Agent, or Firm* — Holtz, Holtz, Goodman & Chick, PC (57) ABSTRACT

A tissue culture microscope apparatus includes a culture unit that includes a chamber in which a specimen is put, and maintains the chamber at a predetermined temperature to culture the specimen; an observation unit that forms an observation image of the specimen put in the chamber; and a liquid supply unit that stores a liquid in a protrusion portion penetrating into a wall of the chamber and protruding to an inside of the chamber, matches a temperature of the liquid with the temperature of the chamber, and injects the liquid from the protrusion portion to the specimen.

30 Claims, 5 Drawing Sheets

TISSUE CULTURE MICROSCOPE APPARATUS

CROSS-REFERENCE TO RELATED APPLICATIONS

This application is based upon and claims the benefit of priority from Japanese Patent Applications No. 2005-276205, filed Sep. 22, 2005; and No. 2006-208876, filed Jul. 31, 2006, the entire contents of both of which are incorporated herein by reference.

BACKGROUND OF THE INVENTION

1. Field of the Invention

The present invention relates to a tissue culture microscope apparatus that allows observation of a cell in culture.

2. Description of the Related Art

There has been a trend for molecular biological or biophysical research to use a cultured cell. The normal indoor environment in which a light microscope is used adversely affects the cell in culture because the cell environment in culture differs from such indoor environment.

A specific tissue cell microscope is reported in which a light microscope and an incubator for maintaining an environment suitable for cell culture are combined together, allowing observation of a cell in culture (see JP-A No. 2006-11415 (KOKAI), for example).

In a cell culture experiment, dosing for the cell is sometimes required. Since an environment suitable for cell culture is maintained within the incubator (cell culture space), dosing through an opening of the incubator results in changes in the cell culture environment and causes a difference in temperature between the specimen and the reagent. As a result, the dosing causes out of focus objects and has temperature effects on the cell.

Using a specific dosing apparatus, which is installed in the incubator, can avoid to change the cell culture environment and to have temperature effects on the cell. However, since frequency of use of the reagent is low, for example, one dosing per experiment, such a specific dosing apparatus provides a low cost-effectiveness. Also, installing the specific dosing apparatus makes the whole incubator complicated and thus makes it hard to clean. Insufficient cleaning makes it easy to get mold.

Operation on a cell in culture, such as dosing, using the conventional apparatus without a change in cell culture environment, when feasible, is beneficial.

SUMMARY OF THE INVENTION

A tissue culture microscope apparatus according to one aspect of the present invention includes a chamber in which a specimen is put, and maintains the chamber at a predetermined temperature to culture the specimen; an observation unit that forms an observation image of the specimen put in the chamber; and a liquid supply unit that stores a liquid in a protrusion portion penetrating into a wall of the chamber and protruding to an inside of the chamber, matches a temperature of the liquid with the temperature of the chamber, and injects the liquid from the protrusion portion to the specimen.

A tissue culture microscope apparatus according to another aspect of the present invention includes a culture unit that includes a chamber in which a specimen is put, and maintains the chamber at a predetermined temperature to culture the specimen; an observation unit that includes an objective lens, and forms an observation image of the specimen put in the chamber through the objective lens; an illumination unit that performs at least one of transmitting illumination and incident-light illumination on the specimen; a moving unit that holds the specimen with a vessel and moves the specimen with respect to the objective lens in three dimensions; and a liquid supply unit that stores a liquid in a protrusion portion penetrating into a wall of the chamber and protruding to an inside of the chamber, matches a temperature of the liquid with the temperature of the chamber, and injects the liquid from the protrusion portion to the specimen.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention will be described below with reference to the accompanying drawings.

Figure 1:
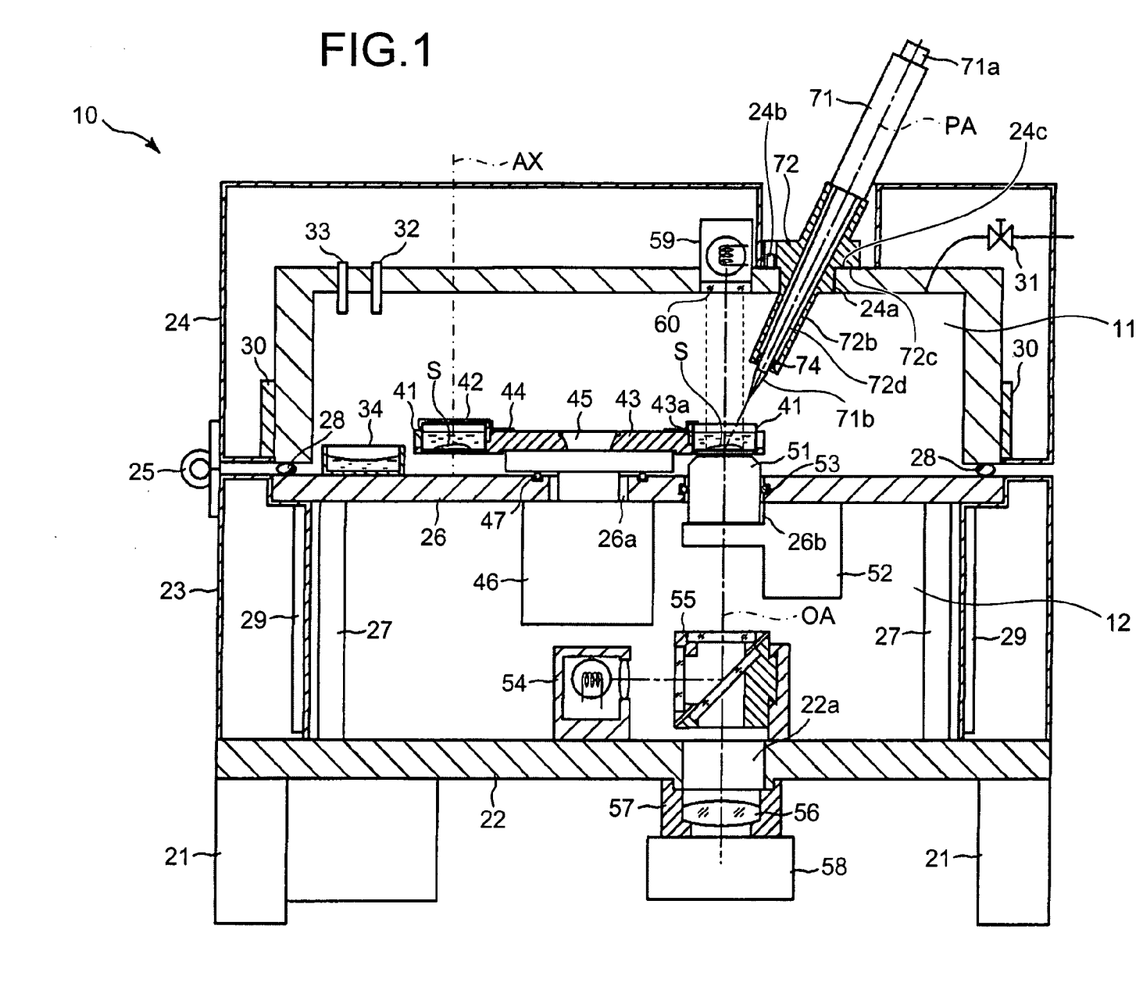
FIG. 1 is a cross-sectional view of a tissue culture microscope apparatus in accordance with the present invention.

FIG. 1 is a cross-sectional view of a tissue culture microscope apparatus in accordance with the present invention. The tissue culture microscope apparatus mainly includes a culture unit allowing control of temperature, humidity, $CO_2$ concentration of a specimen containing a cultured cell; and a microscope allowing enlarged observation of the specimen.

As shown in FIG. 1, the tissue culture microscope apparatus 10 includes a base member 22 supported by feet 21; a closed side wall 23 on the periphery of the base member 22; a separator 26 closing an upper opening of the side wall 23; and an opening/closing cover 24 having a open bottom.

The separator 26 is supported by a plurality of support posts 27 stood on the base member 22. The side wall 23 has a cavity serving as a thermal insulation space, and includes a heater 29 in the cavity.

The opening/closing cover 24 is attached to the side wall 23 by a hinge 25, thereby opening and closing the upper of the closed side wall 23. A sealing member 28 is provided between the opening/closing cover 24 and the separator 26. The opening/closing cover 24 comes in contact with the separator 26 through the sealing member 28 in the closed state, thereby making it airtight between the opening/closing cover 24 and the separator 26. The opening/closing cover 24 also has a cavity serving as a thermal insulation space, and includes a heater 30 in the cavity.

The opening/closing cover 24 is provided with a temperature sensor 32 detecting the temperature inside the culture space; a $CO_2$ sensor 33 detecting the $CO_2$ concentration inside the culture space; and an electromagnetic valve 31 adjusting the $CO_2$ concentration inside the culture space. The culture space is connected to a $CO_2$ source through the electromagnetic valve 31.

The opening/closing cover 24 and the separator 26 constitute a culture chamber 11 housing the specimen. The culture chamber 11 and the closed opening/closing cover 24 forms a closed space (culture space); the closed space is controlled to maintain an environment suitable for a cultured cell S. Specifically, the culture space is controlled to have a temperature of 37° C., a $CO_2$ concentration of 5%, and a humidity of 95%. A member for forming the culture space and a member for controlling the culture space environment are included in the culture unit. The base member 22, the side wall 23, and the separator 26 constitute a buffer chamber 12. The buffer chamber 12 is controlled to maintain an environment with the same temperature and a low humidity compared with the culture chamber 11. Specifically, the buffer chamber 12 is controlled to have a temperature of 37° C. and a humidity of about 50%.

The tissue culture microscope apparatus 10 includes a specimen tray 43 holding a specimen vessel 41 containing the culture cell S and culture media; a tray receiver 45 to which the specimen tray 43 is attached; and a horizontal sliding mechanism 46 horizontally sliding the tray receiver 45.

The specimen tray 43 has a plurality of depressions 43a in which the specimen vessel 41 is placed. The specimen tray 43 has a disk shape; the depressions 43a are spaced on the same circumference at almost regular intervals. Each depression 43a has an opening that allows optical observation from below. The specimen vessel 41 is put in the depression 43a of the specimen tray 43 and fixed by a fixing member 44 being a metal plate. The specimen vessel 41 put in the specimen tray 43 is covered with a vessel cover 42.

The separator 26 has a through hole 26a, and the tray receiver 45 extends through the through hole 26a of the separator 26. The horizontal sliding mechanism 46 is located in the buffer chamber 12. An elastic member 47 is provided between the separator 26 and the tray receiver 45 in order to ensure less moisture leak. A gap of not more than 0.1 mm may be provided between the separator 26 and the tray receiver 45 without the elastic member 47.

The microscope being an observation unit includes an objective lens 51; a focus unit 52 for vertically sliding the objective lens 51; an imaging lens 56; and an imaging device 58.

The separator 26 has a through hole 26b, and the objective lens 51 is penetrated in the separator 26 through the through hole 26b. An elastic member 53 is provided between the separator 26 and the objective lens 51 in order to ensure less moisture leak.

The base member 22 has a through hole 22a. A holder frame 57 is provided in the through hole 22a of the base member 22 to hold the imaging lens 56 and the imaging device 58. The imaging lens 56 and the imaging device 58 are located under the buffer chamber 12, and optically coupled to the objective lens 51 through the through hole 22a of the base member 22.

The microscope also includes an incident-light illumination optical system that is used for fluoroscopy for a specific region using fluorochrome or fluorescent protein of the cultured cell S; and a transmitting illumination optical system for morphological observation for capturing the whole image of the cultured cell S.

The incident-light illumination optical system includes an incident-light source 54 and a fluorescent filter 55 which are both provided in the buffer chamber 12. The fluorescent filter 55 is located between the objective lens 51 and the imaging device 58, reflects the excitation light emitted from the incident-light source 54 to the objective lens 51, and transmits the fluorescence emitted from the cultured cell S to the imaging device 58.

The transmitting illumination optical system includes a transmitting light source 59 and an optical window 60 which are both provided in the inner wall of the opening/closing cover 24 so as to seal the inner wall. The transmitting light source 59 and the optical window 60 are located above the objective lens 51.

In use of the tissue culture microscope apparatus 10, the specimen tray 43 with the specimen vessels 41 held is attached to the tray receiver 45, and a humidifier pad 34 containing pure water is placed in the culture chamber 11. The heaters 29, 30 are controlled based on temperature data detected by the temperature sensor 32, and the electromagnetic valve 31 is controlled based on $CO_2$ concentration data detected by the $CO_2$ sensor 33. The inside of the culture chamber 11 is controlled to have a $CO_2$ concentration of 5% and a temperature of 37° C. The inside of the buffer chamber 12 is controlled to have a temperature of 37° C. The culture chamber 11 is immune to the ambient air due to the thermal insulation space of the opening/closing cover 24. The internal temperature of the culture chamber 11 is stably maintained at 37° C. because the buffer chamber 12 is 37° C. in temperature as well. The inside of the culture chamber 11 is maintained at a high humidity of more than 95% because the moisture in the culture chamber 11 is difficult to leak.

In observation, the specimen vessel 41 located above the objective lens 51 is observed. The specimen vessel 41 to be observed is changed over to another one by rotation of the specimen tray 43 through the horizontal sliding mechanism 46. Sliding the specimen tray 43 in the plane perpendicular to the optical axis of the objective lens 51 by the horizontal sliding mechanism 46 allows adjustment of the observation region in the specimen vessel 41. This adjustment is achieved by a combination of rotation and translation of the specimen tray 43.

Figure 2:
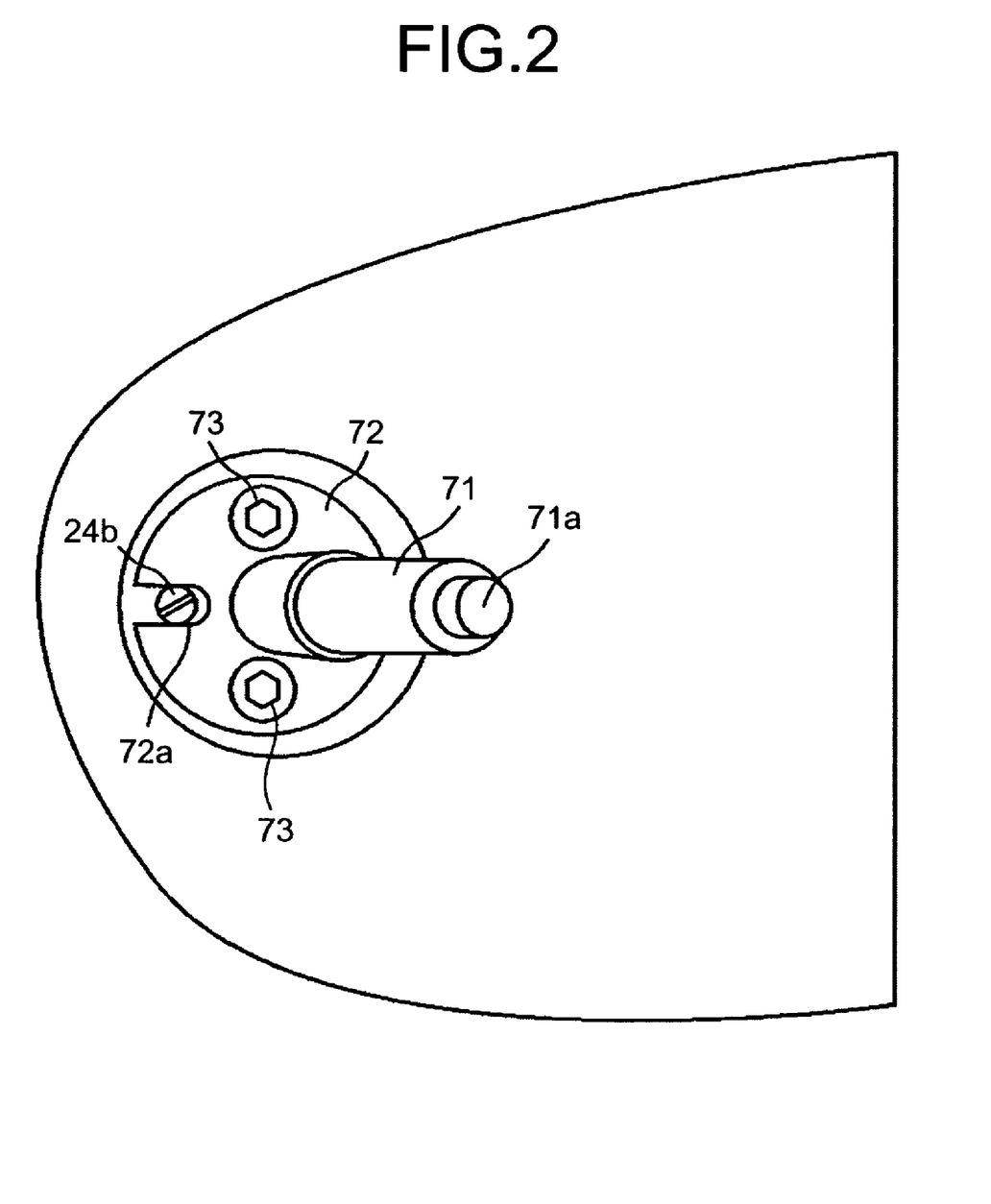
FIG. 2 is a top view of peripheral parts of a pipette shown in FIG. 1.

The opening/closing cover 24 has a through hole 24a in the vicinity of the transmitting light source 59. A holding member 72 being a communication holder is fitted in the through hole 24a. As shown in FIG. 2, the opening/closing cover 24 includes a rotation stopper pin 24b being a positioning member that protrudes upward and positions the holding member 72 in its rotation. The holding member 72 has a groove 72a serving as a position reference engaged with the rotation stopper pin 24b. The holding member 72 has a flange face 72c serving as another position reference. Contact between the flange face 72c and a positioning face 24c begin a positioning member in the height direction of the opening/closing cover 24 sets the height position of the holding member 72. Fitting the rotation stopper pin 24b in the groove 72a sets the rotation position of the holding member 72. The holding member 72 is also secured to the opening/closing cover 24 with two screws 73. In other words, the holding member 72 is detachable from the opening/closing cover 24 and positioned in the opening/closing cover 24.

The holding member 72 has a communication hole 72d communicating the inside of the culture chamber 11 with the outside of the culture chamber 11 and holds a pipette 71 in the communication hole 72d. The pipette 71 serves as a liquid injector for injecting a liquid such as reagent into the specimen vessel 41. The holding member 72 also has a protrusion holder 72b protruding to the inside of the culture chamber 11. The protrusion holder 72b is directed to the cultured cell S located in the optical axis OA of the objective lens 51 when the holding member 72 is attached to the opening/closing cover 24. The commercial pipette 71 generally has a conical or cylindrical shape, and is firmly held by the elastic member 74 with the central axis of the communication hole 72d coinciding with the axis PA of the pipette 71. The elastic member 74 seals a gap between the pipette 71 and the protrusion holder 72b in the communication hole 72d, thereby preventing the moisture inside of the culture chamber 11 from leaking out. The holding member 72 is accurately attached to the opening/closing cover 24 so that the axis PA of the pipette 71 held in the communication hole 72d intersects with the optical axis OA being an observation axis of the microscope. Accordingly, the pipette 71, which is held by the holding member 72, is accurately positioned and secured. The axis PA of the pipette 71 is preferably positioned to intersect with the intersection of the optical axis OA of the microscope coincides and the cultured cell S.

The pipette 71, which is held by the holding member 72 attached to the opening/closing cover 24, stores a liquid such as reagent inside a distal portion 71b protruding to the inside of the culture chamber 11. In other words, the liquid stored in the distal portion 71b of the pipette 71 is located in the culture chamber 11. The pipette 71 has an operating portion 71a for performing an operation such as liquid injection; the operating portion 71a is located outside the culture chamber 11 so as to allow an operation outside the culture chamber 11.

The temperature of the liquid stored in the distal portion 71b, therefore, coincides with the temperature inside the culture chamber 11; the pipette 71 can inject a liquid form the distal portion 71b into the cultured cell S in accordance with an operation of the operating portion 71a outside the culture chamber 11. Consequently, in the tissue culture microscope apparatus 10 in accordance with the embodiment, it is not required to open the opening/closing cover 24 to inject the liquid, and a liquid such as reagent can be injected into the cultured cell S without a change in the culture environment inside the culture chamber 11. Since the injection of liquid can be performed after the temperature of the liquid to be injected coincides with the temperature inside the culture chamber 11, the cultured cell S is not affected by changes in temperature. Further, using the commercial pipette 71, which has a simple structure for attachment, as liquid injection means makes it easy to clean the tissue culture microscope apparatus 10. Since the holding member 72 is detachable from the opening/closing cover 24 and can be repeatedly accurately attached to the same position, the holding member 72 may be replaced with another one having a different shape so as to be suitable for various pipettes.

Figure 3:
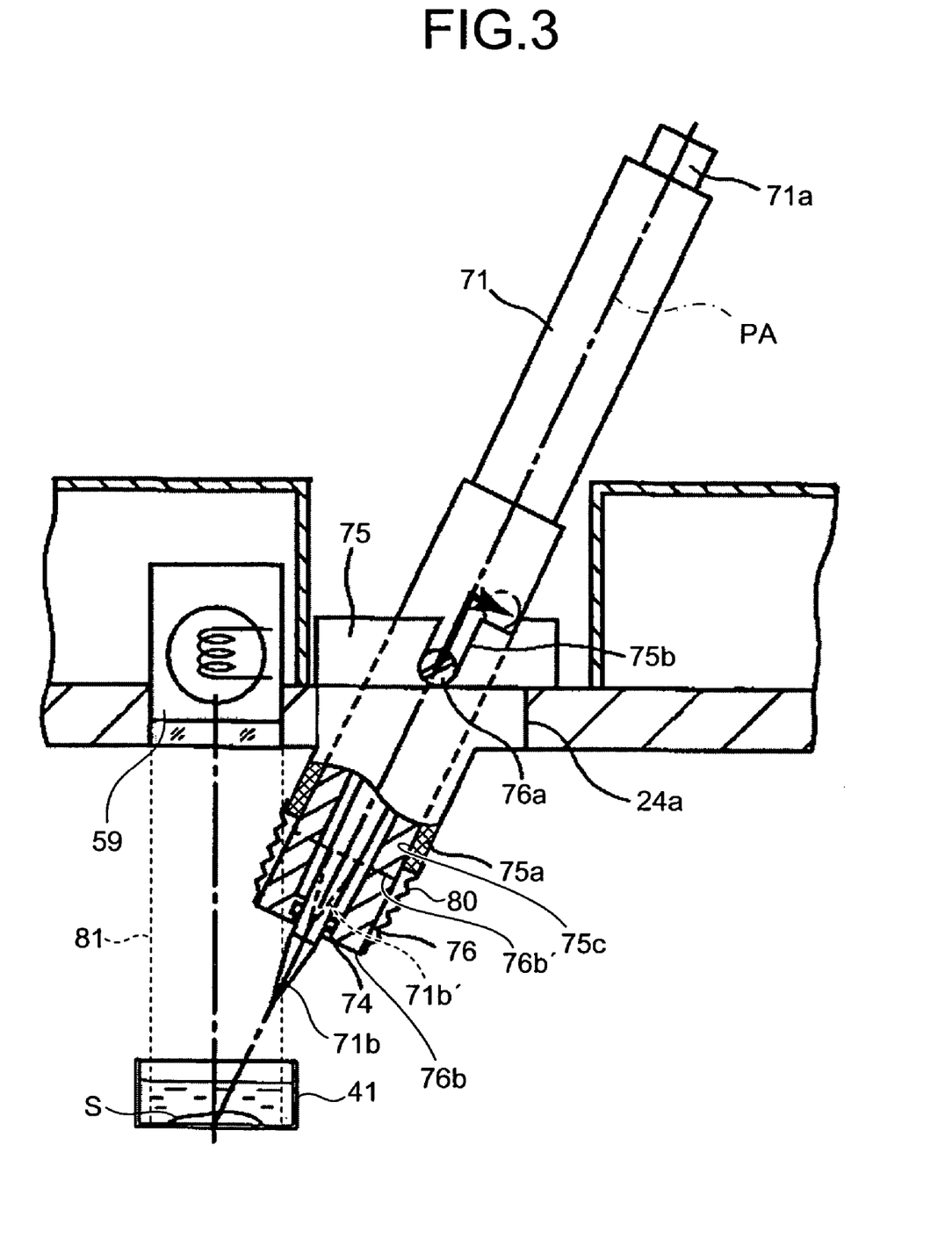
FIG. 3 shows a liquid supply mechanism replaceable with one shown in FIGS. 1 and 2.

FIG. 3 shows a liquid supply mechanism replaceable with one using the pipette 71 and the holding member 72 shown in FIGS. 1 and 2. The liquid supply mechanism includes a holding member 75 fitted in the through hole 24a of the opening/closing cover 24; and a movable member 76 serving as an intermediate holder movably held in the holding member 75. The structure of the holding member 75 for attachment to the opening/closing cover 24 is the same as that of the holding member 72. The holding member 75 includes a protrusion holder 75a protruding to the inside of the culture chamber 11. The protrusion holder 75a is directed to the cultured cell S located in the optical axis OA of the objective lens 51 when the holding member 75 is attached to the opening/closing cover 24. The movable member 76 has a cylindrical shape, and is inserted into a communication hole 75c of the holding member 75 so as to move along the communication hole 75c. A corniced elastic member 80 is provided between the distal portion of the movable member 76 and the distal portion of the protrusion holder 75a. The elastic member 80 seals a gap between the movable member 76 and the protrusion holder 75a in the communication hole 75c, thereby preventing the moisture inside of the culture chamber 11 from leaking out. The movable member 76 includes an elastic member 74 inside its distal portion. The pipette 71 is held so as to be inserted into the movable member 76. The elastic member 74 ensure to hold the axis PA of the pipette 71 with the axis PA coinciding with the central axis of the movable member 76. The elastic member 74 also seals a gap between the pipette 71 and the movable member 76, thereby preventing the moisture inside of the culture chamber 11 from leaking out.

The holding member 75 has a U-shaped groove 75b that is formed by cutting the holding member 75 from the upper end along the central axis. The movable member 76 serving as an inserted member inserted into the communication hole 75c includes a pin 76a protruding from its external surface. The movable member 76 is positioned along the central axis of the communication hole 75c at two positions: one position where the pin 76a is engaged with the groove 75b at the bottom of the groove 75b, and another position where the pin 76a is out of the groove 75b at the shoulder of the groove 75b. Accordingly, the pipette 71 can be positioned so that the distal portion 71b of the pipette 71 is near or away from the specimen vessel 41. Specifically, when the pin 76 is engaged with the bottom of the groove 75b, the distal portion 71b of the pipette 71 is located near the cultured cell S in the optical path 81 of the transmitting light source 59 in the transmitting illumination optical system; when the pin 76 is at the shoulder of the groove 75b, the distal portion 71b and the distal portion 76b of the movable member 76 are out of the optical path 81, as a distal portion 71b' and a distal portion 76b', respectively, in FIG. 3 for example. Consequently, the distal portion 71b of the pipette 71 is located near the cultured cell S in liquid injection, and located away from the cultured cell S in observation without obscuring the transmitting illumination light.

Figure 4:
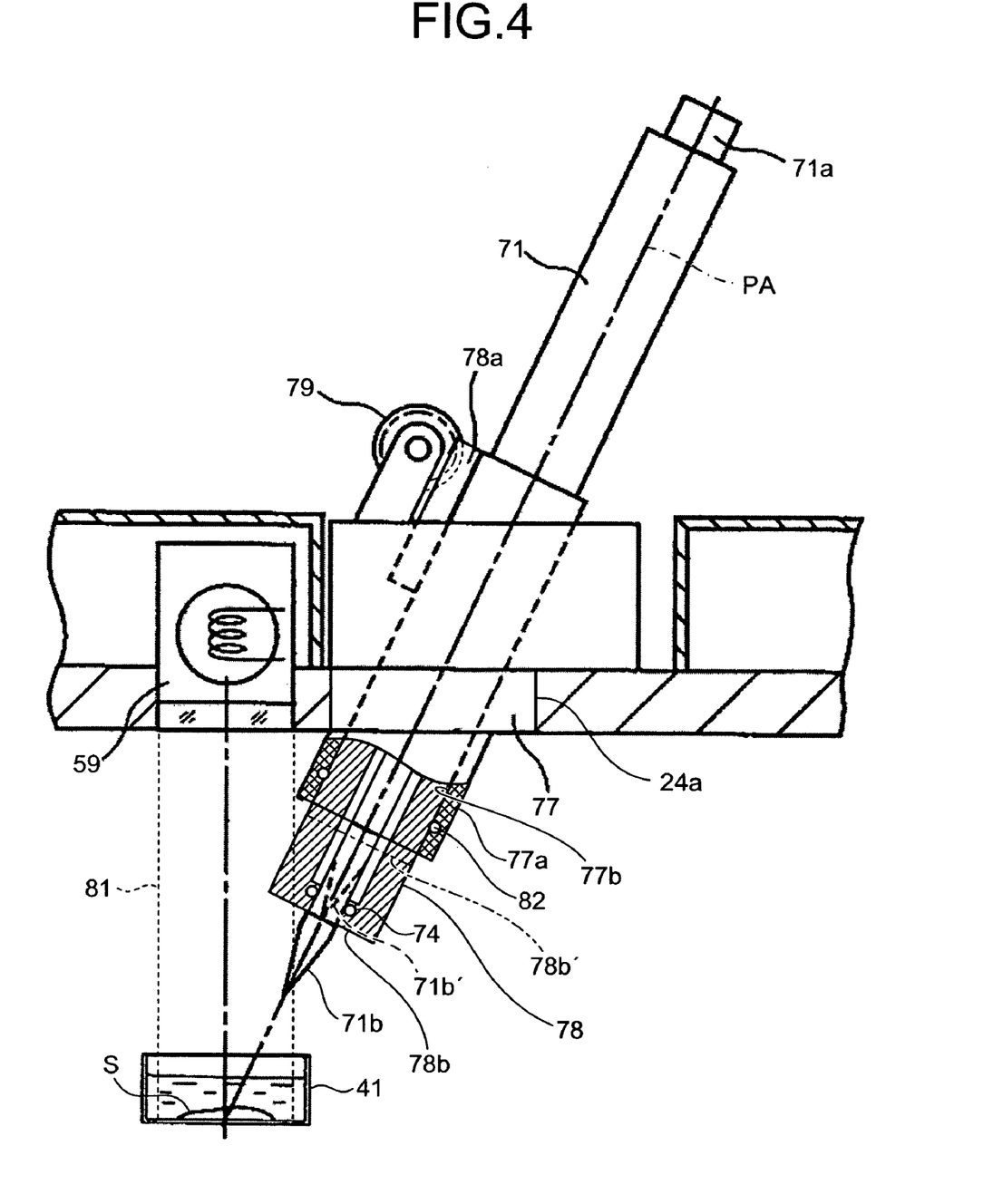
FIG. 4 shows another liquid supply mechanism replaceable with one shown in FIGS. 1 and 2.

FIG. 4 shows another liquid supply mechanism replaceable with one using the pipette 71 and the holding member 72 shown in FIGS. 1 and 2. This liquid supply mechanism includes a holding member 77 fitted in the through hole 24a of the opening/closing cover 24; and a movable member 78 serving as an intermediate holder movably held in the holding member 77. The structure of the holding member 77 for attachment to the opening/closing cover 24 is the same as that of the holding member 72. The holding member 77 includes a protrusion holder 77a protruding to the inside of the culture chamber 11. The protrusion holder 77a is directed to the cultured cell S located in the optical axis OA of the objective lens 51 when the holding member 77 is attached to the opening/closing cover 24. The movable member 78 has a cylindrical shape, and is inserted into a communication hole 77b of the holding member 77 so as to move along the communication hole 77b. The protrusion holder 77a includes an elastic member 82 inside its distal portion. The elastic member 82 seals a gap between the movable member 78 and the protrusion holder 77a in the communication hole 77b, thereby preventing the moisture inside of the culture chamber 11 from leaking out. The movable member 78 includes an elastic member 74 inside its distal portion. The pipette 71 is held so as to be inserted into the movable member 78. The elastic member 74 ensure to hold the axis PA of the pipette 71 with the axis PA coinciding with the central axis of the movable member 78. The elastic member 74 also seals a gap between the pipette 71 and the movable member 78, thereby preventing the moisture inside of the culture chamber 11 from leaking out.

The movable member 78 serving as an inserted member inserted into the communication hole 77b includes a rack 78a at its external surface. The holding member 77 includes a pinion 79 engaged with the rack 78a. The movable member 78 is moved along the central axis of the communication hole 77b according to rotation operation of the pinion 79. In other words, rotating the pinion 79 allows the distal portion 71b of the pipette 71 to be positioned near or away from the specimen vessel 41. Specifically, in FIG. 4, when the pinion 79 is rotated clockwise, the distal portion 71b of the pipette 71 is positioned near the cultured cell S in the optical path 81 of the transmitting light source 59 in the transmitting illumination optical system; when the pinion 79 is rotated counterclockwise, the distal portion 71b and the distal portion 78b of the movable member 78 are out of the optical path 81, as a distal portion 71b' and a distal portion 78b', respectively, for example. Consequently, the distal portion 71b of the pipette 71 is located near the cultured cell S in liquid injection, and located away from the cultured cell S in observation without obscuring the transmitting illumination light. The positioning mechanism using the rack 78a and the pinion 79 allows accurate adjustment of the position of the movable member 78.

Figure 5:
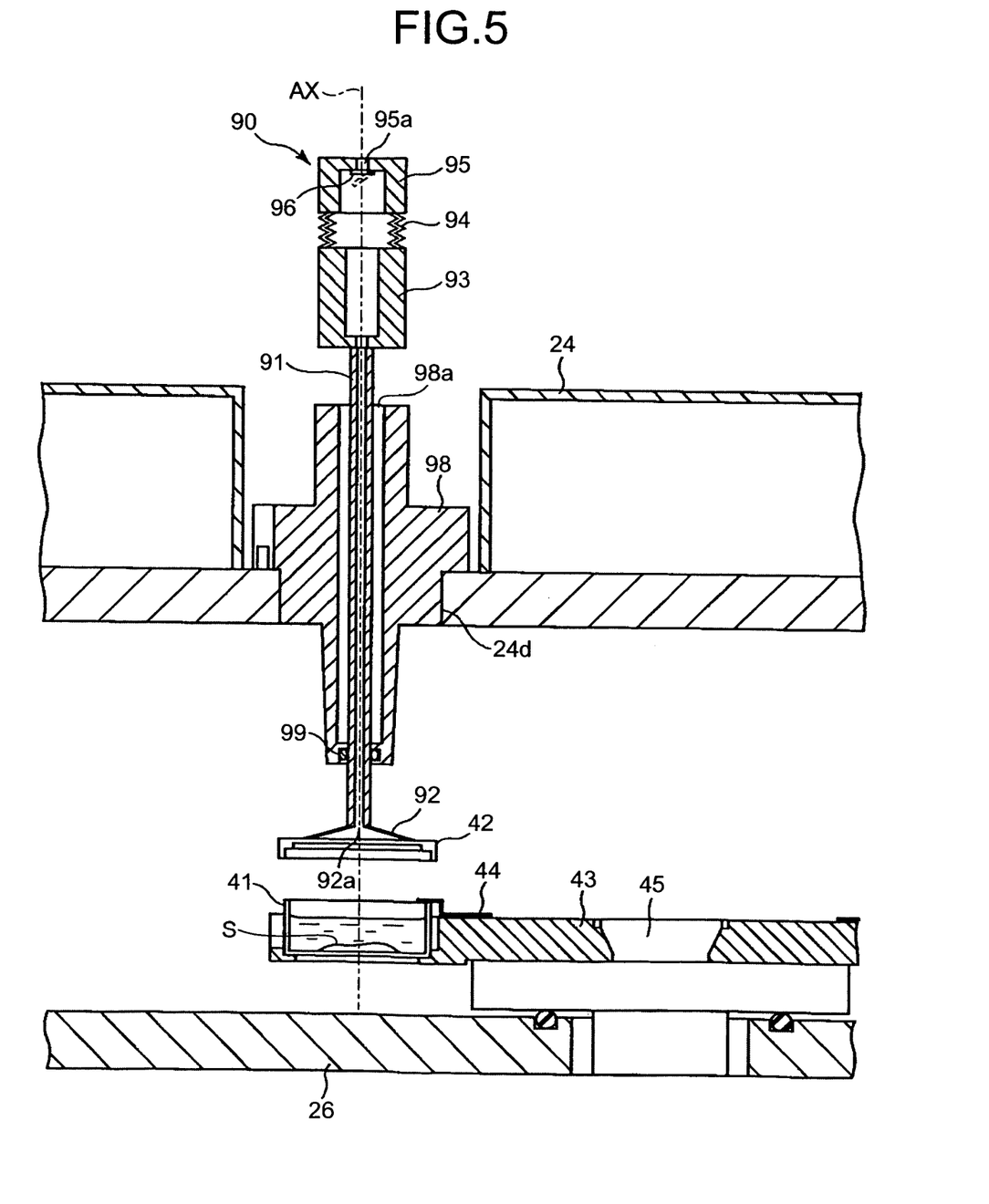
FIG. 5 is a detachable mechanism for attaching/detaching a vessel cover to/from a specimen vessel.

The tissue culture microscope apparatus 10 in accordance with the embodiment may include an attaching/detaching mechanism that attaches/detaches a vessel cover 42 for covering the upper opening of the specimen vessel 41. FIG. 5 shows the attaching/detaching mechanism arranged in the axis AX shown in FIG. 1. The axis AX intersects with the optical axis OA of the objective lens 51, i.e., the center of the specimen vessel 41 that has been moved to a position which is out of the optical path 81. Referring to FIG. 1, the axis AX is located in the cross-sectional view corresponding to the drawing sheet. However, the axis AX may be located at any position which is out of the optical path 81.

As shown in FIG. 5, the opening/closing cover 24 has a through hole 24d in a wall portion (ceiling surface) which is above a position to which the specimen vessel 41 is moved. A holding member 98 is penetrated in the through hole 24d. The holding member 98 serves as a holder that holds an adhesive device 90 for capturing the vessel cover 42. The structure of the holding member 98 for attachment to the opening/closing cover 24 is the same as that of the holding member 72. The holding member 98 has a communication hole 98a communicating the inside of the culture chamber 11 with the outside of the culture chamber 11 in parallel with the axis AX. An elastic member 99 is provided inside the lower portion of the communication hole 98a.

The adhesive device 90 includes a cylindrical communication pipe 91 inserted into the communication hole 98a; an adhesive disk 92 secured to the lower end of the communication pipe 91; a cylindrical operating portion 93 secured to the upper end of the communication pipe 91; and an operation button 95 secured to the upper end of the operating portion 93 through a corniced elastic member 94. The adhesive disk 92 is made of elastic material, and has a cup shape. The adhesive disk 92 also has an opening 92a at its center. The communication pipe 91, the operating portion 93, the elastic member 94, and operation button 95 are connected through their internal spaces, and connected to the internal space of the culture chamber 11 through the opening 92a of the adhesive disk 92. The operation button 95 has an opening 95a, which includes a valve 96. The communication pipe 91 comes into contact with the holding member 98 through the elastic member 99. The elastic member 99 holds the adhesive device 90 so that the adhesive device 90 moves vertically. The elastic member 99 also seals a gap between the communication pipe 91 and the holding member 98 in the communication hole 98a, thereby preventing the moisture inside of the culture chamber 11 from leaking out.

The vessel cover 42 is removed as follows. The specimen vessel 41 covered with the vessel cover 42 is first placed right below the adhesive device 90. The adhesive device 90 is then pushed down by pushing the operation button 95 with the elastic member 94 compressed, in order to make the adhesive disk 92 and the vessel cover 42 stick. After that, the operation button 95 is released. Here, since the elastic member 94 is returned to its original shape, a space between the vessel cover 42 and the adhesive disk 92 is under negative pressure through the communication pipe 91, so that the vessel cover 42 sticks to the adhesive disk 92. Finally, the adhesive device 90 is pulled up. The specimen vessel 41 is moved in place by rotation of the specimen tray 43 through the horizontal sliding mechanism 46, which allows the liquid injection.

The specimen vessel 41 is covered with the vessel cover 42 as follows. The specimen vessel 41 is first placed right under the vessel cover 42 held by the adhesive device 90. The adhesive device 90 is then pushed down in order to cover the specimen vessel 41 with the vessel cover 42. After that, the valve 96 is opened. Here, since the internal space of the adhesive device 90 is returned to atmospheric pressure, the adsorption due to the adhesive disk 92 is released by the weight of the vessel cover 42.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A tissue culture microscope apparatus which holds a liquid injector that is adapted to store and inject a liquid according to a predetermined operation, the apparatus comprising:
    a culture unit that includes a chamber adapted to house a specimen, and that maintains the chamber at a predetermined temperature to culture the specimen;
    an observation unit that is adapted to form an observation image of the specimen housed in the chamber; and
    a communication holder that is detachable from a wall of the chamber and that includes: (i) a protrusion portion penetrating into the wall of the chamber, (ii) a communication hole formed in the protrusion portion and communicating an inside of the chamber with an outside of the chamber, and (iii) a sealing member formed in the protrusion portion and sealing a gap formed between the liquid injector and the communication holder in the communication hole between the inside of the chamber and the outside of the chamber,
    wherein the communication holder is adapted to hold the liquid injector in the communication hole such that: (i) a temperature of the liquid in the liquid injector is matched with the predetermined temperature of the chamber, and (ii) the liquid injector is held in an inclined state and injects the liquid from the protrusion portion to the specimen, and
    wherein the communication holder further includes an intermediate holder that: (i) is adapted to hold the liquid injector, (ii) penetrates the communication hole, and (iii) is movably held along the communication hole while maintaining a sealed state between the liquid injector and the communication holder in the communication hole.

2. The tissue culture microscope apparatus according to claim 1, wherein the sealing member seals the gap between the liquid injector and the communication holder in the communication hole when the liquid injector penetrates into the communication hole.

3. The tissue culture microscope apparatus according to claim 2, wherein the sealing member is made of elastic material.

4. The tissue culture microscope apparatus according to claim 1, further comprising an external operating portion for performing the predetermined operation outside the chamber when the liquid injector is held in the communication hole.

5. The tissue culture microscope apparatus according to claim 1, wherein the communication holder penetrates into the wall with the communication hole directed to the specimen, and is adapted to hold the liquid injector with a distal portion of the liquid injector directed to the specimen.

6. The tissue culture microscope apparatus according to claim 5, wherein the communication holder is adapted to hold the liquid injector so that an axis of the liquid injector is directed to an intersection between an observation axis of the observation unit and the specimen.

7. The tissue culture microscope apparatus according to claim 1, wherein the communication holder has a position reference portion for the wall, penetrates into the wall with the position reference portion coming into contact with a positioning member formed on the wall, and is detachable from the wall.

8. The tissue culture microscope apparatus according to claim 7, wherein a position of rotation of the communication holder is positioned by the position reference portion.

9. The tissue culture microscope apparatus according to claim 1, wherein the communication holder is adapted to hold the liquid injector so as to be detachable from the communication hole.

10. The tissue culture microscope apparatus according to claim 1, further comprising an illumination unit that is adapted to illuminate the specimen from a side of the communication holder with respect to the specimen,
wherein the communication holder holds the intermediate holder at one of a first position and a second position along the communication hole, positions a distal portion of the liquid injector near the specimen in an optical path of the illumination unit when the intermediate holder is held at the first position, and positions the distal portion of the liquid injector out of the optical path when the intermediate holder is held at the second position.

11. The tissue culture microscope apparatus according to claim 10, wherein:
the intermediate holder has an inserted portion adapted to hold the liquid injector and inserted into the communication hole, and a protrusion portion protruding from an external surface of the inserted portion, and
the communication holder has a U-shaped groove in a side of the communication hole, holds the intermediate holder at the first position by engaging the protrusion portion with a first end of the groove, and holds the intermediate holder at the second position by positioning the protrusion portion at a second end of the groove, the first end being near the chamber, the second end being away from the chamber out of the groove.

12. The tissue culture microscope apparatus according to claim 10, wherein:
the intermediate holder includes: (i) an inserted portion adapted to hold the liquid injector and inserted into the communication hole; and (ii) a rack secured to an external surface of the inserted portion, and
the communication holder includes a pinion which is located at a position facing the rack when the inserted portion is inserted into the communication hole, and holds the intermediate holder at the one of the first position and the second position by rotating the pinion engaged with the rack.

13. The tissue culture microscope apparatus according to claim 1, wherein the sealing member comprises a first sealing member to seal a gap between the liquid injector and the intermediate holder in the communication hole, and a second sealing member to seal a gap between the intermediate holder and the communication hole, when the intermediate holder is inserted into the communication hole.

14. The tissue culture microscope apparatus according to claim 1, further comprising an attaching/detaching mechanism that attaches/detaches a cover to/from a vessel adapted to hold the specimen at a bottom thereof in the chamber according to a predetermined attaching/detaching operation, wherein the attaching/detaching mechanism includes an attaching/detaching operating portion that penetrates into the wall of the chamber and allows performance of the predetermined attaching/detaching operation outside the chamber, and wherein the cover covers an upper opening of the vessel.

15. The tissue culture microscope apparatus according to claim 14, further comprising a sliding unit that slides the vessel in a direction perpendicular to an observation axis of the observation unit in the chamber,
wherein the attaching/detaching mechanism attaches/detaches the cover to/from the vessel that has been slid by the sliding unit to a position which is out of the observation axis.

16. The tissue culture microscope apparatus according to claim 14, wherein the attaching/detaching mechanism includes:
a cylindrical communication pipe;
a cup-like adhesive disk that is provided at one end of the communication pipe and that is adapted to come into contact with the cover;
an air pressure controller that is provided at another end of the communication pipe and controls an air pressure inside a space formed between the cover and the adhesive disk through the communication pipe;
a holder that penetrates into the wall of the chamber, communicates the inside of the chamber with the outside of the chamber through a communication hole, holds the communication pipe penetrating into the communication hole so that the communication pipe is movable along the communication hole, and holds the adhesive disk and the air pressure controller respectively inside and outside the chamber through the communication pipe; and
a sealing member that seals a gap between the communication pipe and the holder,
wherein the adhesive disk holds the cover based on a pressure reducing operation in the air pressure controller, and releases the held cover based on a pressure increasing operation in the air pressure controller.

17. The tissue culture microscope apparatus according to claim 1, wherein the liquid injector is an independent element.

18. The tissue culture microscope apparatus according to claim 1, wherein the predetermined temperature of the chamber is 37° C., and
wherein, in the chamber, a $CO_2$ concentration is controlled to be 5%, and humidity is controlled to be 95%, and a temperature in a buffer chamber housing the observation unit is controlled to substantially be 37° C., and humidity in the buffer chamber is controlled to approximately be 50%.

19. The tissue culture microscope apparatus according to claim 1, further comprising another sealing member for sealing a gap between the intermediate holder and the liquid injector held by the intermediate holder, wherein the sealed state between the liquid injector and the communication holder in the communication hole is maintained by the sealing of said sealing member and said another sealing member.

20. A tissue culture microscope apparatus which holds a liquid injector that is adapted to store and inject a liquid according to a predetermined operation, the apparatus comprising:
- a culture unit that includes a chamber adapted to house a specimen, and that maintains the chamber at a predetermined temperature to culture the specimen;
- an observation unit that includes an objective lens, and that is adapted to form an observation image of the specimen housed in the chamber through the objective lens;
- an illumination unit that is adapted to perform at least one of transmitting illumination and incident-light illumination on the specimen;
- a moving unit that is adapted to hold the specimen in a vessel and move the specimen with respect to the objective lens in three dimensions; and
- a communication holder that is detachable from a wall of the chamber and that includes: (i) a protrusion portion penetrating into the wall of the chamber, (ii) a communication hole formed in the protrusion portion and communicating an inside of the chamber with an outside of the chamber, and (iii) a sealing member formed in the protrusion portion and sealing a gap formed between the liquid injector and the communication holder in the communication hole between the inside of the chamber and the outside of the chamber,
- wherein the communication holder is adapted to hold the liquid injector in the communication hole such that: (i) a temperature of the liquid in the liquid injector is matched with the predetermined temperature of the chamber, and (ii) the liquid injector is held in an inclined state and injects the liquid from the protrusion portion to the specimen, and
- wherein the communication holder further includes an intermediate holder that: (i) is adapted to hold the liquid injector, (ii) penetrates the communication hole, and (iii) is movably held along the communication hole while maintaining a sealed state between the liquid injector and the communication holder in the communication hole.

21. The tissue culture microscope apparatus according to claim 20, wherein the sealing member is adapted to seal the gap between the liquid injector and the communication holder in the communication hole when the liquid injector penetrates into the communication hole, and
wherein the communication holder has a position reference member for the wall, penetrates into the wall with the position reference member coming into contact with a positioning member formed on the wall so that the communication hole is directed to the specimen, and wherein the communication holder is adapted to hold the liquid injector so that a distal portion of the liquid injector is directed to the specimen.

22. The tissue culture microscope apparatus according to claim 20, wherein the liquid injector is an independent element.

23. The tissue culture microscope apparatus according to claim 20, wherein the predetermined temperature of the chamber is 37° C., and wherein, in the chamber, a $CO_2$ concentration is controlled to be 5%, and humidity is controlled to be 95%, and a temperature in a buffer chamber housing the observation unit is controlled to substantially be 37° C., and humidity in the buffer chamber is controlled to approximately be 50%.

24. The tissue culture microscope apparatus according to claim 20, wherein the sealing member comprises a first sealing member to seal a gap between the liquid injector and the intermediate holder in the communication hole, and a second sealing member to seal a gap between the intermediate holder and the communication hole, when the intermediate holder is inserted into the communication hole.

25. The tissue culture microscope apparatus according to claim 20, further comprising another sealing member for sealing a gap between the intermediate holder and the liquid injector held by the intermediate holder, wherein the sealed state between the liquid injector and the communication holder in the communication hole is maintained by the sealing of said sealing member and said another sealing member.

26. A tissue culture microscope apparatus which holds a liquid injector that is adapted to store and inject a liquid according to a predetermined operation, the apparatus comprising:
- a culture unit that includes a chamber adapted to house a specimen, and that maintains the chamber at a predetermined temperature to culture the specimen;
- an observation unit that includes an objective lens, and that is adapted to form an observation image of the specimen housed in the chamber through the objective lens;
- a separator that separates the observation unit which is arranged below the culture unit;
- an illumination unit that is arranged on an optical axis of the objective lens and above the specimen, and that is adapted to perform transmitting illumination;
- a moving unit that is adapted to hold the specimen in a vessel and move the specimen with respect to the objective lens in three dimensions; and
- a communication holder that is detachable from an upper portion of a wall of the chamber and that includes: (i) a protrusion portion penetrating into the wall of the chamber, (ii) a communication hole formed in the protrusion portion and communicating an inside of the chamber with an outside of the chamber, and (iii) a sealing member formed in the protrusion portion and sealing a gap formed between the liquid injector and the communication holder in the communication hole between the inside of the chamber and the outside of the chamber,
- wherein the communication holder includes the liquid injector which is provided in the communication hole,
- wherein the communication holder holds the liquid injector such that the liquid injector is inclined with respect to the optical axis of the objective lens and such that a central axis of the held liquid injector intersects with the optical axis of the objective lens at a position of the specimen in the chamber, wherein the liquid injector is movable away from the specimen so as not to interrupt the transmitting illumination during observation, and
- wherein the communication holder further includes an intermediate holder that: (i) is adapted to hold the liquid injector, (ii) penetrates the communication hole, and (iii) is movably held along the communication hole while maintaining a sealed state between the liquid injector and the communication holder in the communication hole.

27. The tissue culture microscope apparatus according to claim 26, wherein the predetermined temperature of the chamber is 37° C.,
   wherein, in the chamber, a $CO_2$ concentration is controlled to be 5%, and humidity is controlled to be 95%, and
   wherein a temperature of the liquid in the liquid injector is made 37° C. by the holding of a distal portion of the liquid injector inside the chamber.

28. The tissue culture microscope apparatus according to claim 26, wherein a temperature in a buffer chamber housing the observation unit is controlled to substantially be 37° C., and humidity in the buffer chamber is controlled to approximately be 50%.

29. The tissue culture microscope apparatus according to claim 26, wherein the sealing member comprises a first sealing member to seal a gap between the liquid injector and the intermediate holder in the communication hole, and a second sealing member to seal a gap between the intermediate holder and the communication hole, when the intermediate holder is inserted into the communication hole.

30. The tissue culture microscope apparatus according to claim 26, further comprising another sealing member for sealing a gap between the intermediate holder and the liquid injector held by the intermediate holder, wherein the sealed state between the liquid injector and the communication holder in the communication hole is maintained by the sealing of said sealing member and said another sealing member.

* * * * *